US006723305B2

(12) United States Patent
DePierro et al.

(10) Patent No.: US 6,723,305 B2
(45) Date of Patent: Apr. 20, 2004

(54) ANTI-MICROBIAL BREATH FRESHENING MOUTHRINSE

(75) Inventors: Karen J. DePierro, Piscataway, NJ (US); Lisa Christina-Beck, Clinton, NJ (US); Hollandra P. Niles, Somerset, NJ (US); Nuran Nabi, Cranbury, NJ (US); Alexander J. Simone, Somerset, NJ (US); John P. Curtis, Alpha, NJ (US)

(73) Assignee: Colgate Palmolive Company, New York, NY (US)

( * ) Notice: Subject to any disclaimer, the term of this patent is extended or adjusted under 35 U.S.C. 154(b) by 0 days.

(21) Appl. No.: 10/358,710

(22) Filed: Feb. 5, 2003

(65) Prior Publication Data

US 2003/0165439 A1 Sep. 4, 2003

Related U.S. Application Data

(60) Provisional application No. 60/361,511, filed on Mar. 4, 2002.

(51) Int. Cl.$^7$ .................................................. A61K 7/16
(52) U.S. Cl. ......................................... 424/54; 424/49
(58) Field of Search ..................................... 424/49–58

(56) References Cited

U.S. PATENT DOCUMENTS

| 4,416,867 | A | | 11/1983 | Ritchey et al. | |
| 4,689,214 | A | * | 8/1987 | Niles et al. | 424/49 |
| 4,814,163 | A | * | 3/1989 | Barth | 424/48 |
| 4,814,164 | A | * | 3/1989 | Barth | 424/48 |
| 5,302,373 | A | | 4/1994 | Giacin et al. | |
| 5,405,604 | A | * | 4/1995 | Hall | 424/54 |
| 5,405,836 | A | * | 4/1995 | Richar et al. | 424/442 |
| 5,681,549 | A | * | 10/1997 | McLaughlin et al. | 424/54 |
| 5,686,063 | A | * | 11/1997 | McLaughlin et al. | 424/54 |
| 6,030,605 | A | * | 2/2000 | D'Amelia et al. | 424/440 |
| 6,197,288 | B1 | * | 3/2001 | Mankoo | 424/49 |
| 6,344,184 | B1 | * | 2/2002 | Rolla | 424/54 |
| 6,479,038 | B1 | * | 11/2002 | Day | 424/49 |

FOREIGN PATENT DOCUMENTS

| WO | WO 90/15592 | 12/1990 | A61K/7/22 |
| WO | WO 00/51559 | 9/2000 | A61K/7/16 |

OTHER PUBLICATIONS

Van Steenberghe, Daniel et al: "Effect of Different Mouthrinses on Morning Breath"; Journal of Periodontology, vol. 72, No. 9, Sep. 2001 pages 1184; tables 1–3–pages 1189.

* cited by examiner

Primary Examiner—Shep K. Rose
(74) Attorney, Agent, or Firm—Bernard Lieberman

(57) ABSTRACT

It has been found that a mouthrinse comprising CPC and zinc ions is a very effective mouthrinse. It has an antibacterial effect that removes odor creating bacteria from the oral cavity. The CPC and zinc ions preferably are used in combination with an ionone terpene such as alpha ionone or a beta ionone.

11 Claims, No Drawings

ANTI-MICROBIAL BREATH FRESHENING MOUTHRINSE

This application claims the benefit of Provisional Application No. 60/362,511, filed Mar. 4, 2002.

FIELD OF THE INVENTION

This invention relates to an anti-microbial breath freshening mouthrinse that contains cetylpyridinium chloride (abbreviated herein to "CPC") and zinc ion. More particularly the invention relates to a mouthrinse that contains CPC and zinc ion and an ionone terpene ketone.

BACKGROUND OF THE INVENTION

It has been known that a mouthrinse composition that contains zinc ions and alpha or beta ionone terpene is effective to reduce mouth odor in humans. This is discussed in U.S. Pat. No. 4,689,214. The zinc ion is provided by a non-toxic organic zinc or inorganic zinc compound. These compositions are effective in counteracting breath odors. However, it has been found that mouthrinse compositions that contain CPC and zinc ions, and in particular zinc acetate have an improved affect in providing fresher breath. This composition can also contain alpha or beta ionone terpenes for additional counteracting of breath odors. However, it is a synergistic anti-microbial effect of CPC and zinc ions that is most effective in providing fresher breath.

BRIEF SUMMARY OF THE INVENTION

A new mouthrinse containing cetylpridinium and zinc salt (CPC/Zn) significantly reduced mouthodor scores caused by volatile sulfur compounds in clinical studies versus a control rinse. It also can contain an ionone terpene. This investigation examined the antimicrobial effects of these rinses in laboratory and clinical studies. Laboratory tests were performed with oral bacteria with alamar blue, a redox dye that rapidly detects bacterial viability. A Treatment of *A. viscosus*, *S. sanguis*, and *S. mutans* by CPC/Zn resulted in a 25, 35 and 16% decrease in bacterial viability respectively versus a control In one study a randomized, double blind clinical study with volunteer subjects was conducted to confirm these laboratory results. After a washout phase, the subjects abstained from oral hygiene and provided a saliva sample for determining the total and oral odorigenic producing bacteria on enriched and indicator plates. Mouthrinses were used once and the subjects sampled at 90 and 180 minutes post treatment for total and oral odorigenic bacteria. In a comparison to a control, the decrease of total bacteria following CPC/Zn use at 90 and 180 minutes were 59.9% and 32.1% respectively. The use of CPC/Zn resulted in 61.7% and 72.5% decrease of odorigenic bacteria at 90 and 180 minutes respectively versus a control rinse. The decrease in bacteria with a CPC/Zn rinse was significantly higher than the control rinse at all post-use time points.

DETAILED DESCRIPTION OF THE INVENTION

There are various strains of bacteria that are present in the mouth. Many of these aid in the production of volatile sulfur compounds that cause mouth odor. These include the following bacteria:

*Actinobacillus*
*Actinomycetemitans*
*Campylobacter recta*
*Capnocytophaga sp.*
*Eikenella corrodens*
*Fusobacterium nucleatum*
*Porphyromonas gingivalis*
*Prevotella intermedia*
*Actinomyces naeslundii*
*Actinomyces viscous*
*Actinomyces mutans*
*Streptococcus mutans*
*Streptococcus sanguis*

For a mouthrinse the CPC will be in the mouthrinse composition in an amount of about 0.0005 percent to about 3 percent by weight, and preferably about 0.01 percent to about 1 percent by weight, The primary component of such a mouthwash usually will be water.

In accordance with a preferred embodiment, this invention relates to an oral composition consisting essentially of a non-toxic zinc compound, usually with salt, in an amount which provides at least about 0.01 mg of zinc ions in 1 ml of water. The ratio of zinc ions to the CPC being about 100:1 to 2:1 by weight, and preferably about 50:1 to about 4:1 by weight.

The zinc compounds that provide zinc ions for use in combination with the CPC may be any physiologically acceptable zinc compound including water soluble (inclusive of sparingly water soluble) organic and inorganic zinc compounds. The water-soluble zinc compounds (at least 1% soluble) are preferred. Examples of suitable zinc compounds that may be employed include:

| | |
|---|---|
| zinc acetate | zinc fluoride |
| zinc ammonium sulfate | zinc formate |
| zinc bromide | zinc iodide |
| zinc chloride | zinc nitrate |
| zinc chromate | zinc phenol sulfonate |
| zinc citrate | zinc salicylate |
| zinc dithionate | zinc sulfate |
| zinc fluosilicate | zinc gluconate |
| zinc tartarate | zinc succinate |
| zinc glycerophosphate | |

Other zinc compounds disclosed in U.S. Pat. No. 4,138,477 having a solubility of a least about 0.01 mg of zinc ions per ml water are incorporated by reference.

The zinc compounds is present in amounts which provides about 0.01–5% by weight of zinc ions and preferably about 0.02–1% of zinc ions by weight in the oral composition.

The mouthrinse composition preferably also will contain an alpha or beta ionone terpene. Ionone is a ketone terpene derivative containing one ketonic carbonyl group. The basic ionone formula is $(CH_3)_3(C_6H_6)_2(CH\ CO\ CH_3)_3$. It is available as alpha-ionone (b.p. 120 degree. C.) and beta-ionone (b.p. 135.degree.), both of which are colorless liquids and slightly soluble in water. It is employed in oral compositions in amounts such that the ratio of zinc ions to ionone is about 1,000:1 to 10:1 by weight. Other variants of ionone such as gamma-ionone dihydroionone and alphamethyl ionone may also be employed. These include isomeric forms of ionones, e.g. irone. It is convenient to employ it in oral compositions in amounts of about 0.0005–1% by weight, preferably about 0.001–1%. Alpha-ionone is the preferred mouthrinse ionone variant.

Any suitable flavoring or sweetening materials may be employed in the mouthrinse or other composition. The presence of flavoring oil improves the taste of the zinc-containing product. Examples of suitable supplemental flavoring oils include oils of spearmint, peppermint, wintergreen, sassafras, clove, sage eucalyptus, marjoram, cinnamon, lemon and orange, as well as methylsalicylate. Mint oils such as oil of peppermint is most preferred.

Suitable sweetening agents include sucrose, lactose, maltose, sorbitol, sodium cyclamate, saccharine, acetosulfam, N-1 alpha.-aspartyl-1-phenylalanine-methyl ester ("aspartame"), xylitol, chalcone materials. Suitably, flavor and sweetening agents may together comprise from about 0.01 to 5% by weight or more of the compositions of the instant invention, each typically being about 0.005–2.5%.

A fluorine-containing compound having a beneficial effect on the care and hygiene of the oral cavity, e.g., diminution of enamel solubility in acid and protection of the teeth against decay may also be incorporated in the composition. Examples thereof include sodium fluoride, potassium fluoride, potassium stannous fluoride ($SnF_2$—KF), sodium hexafluorostannous, stannous chloroflouride, sodium fluorozirconate, and sodium monofluorophosphate. These materials, which disassociate or release fluorine-containing ions in water, suitably may be present in an effective but non-toxic amount, usually within the range of about 0.01 to 1% by weight of the water-soluble fluorine content thereof.

When the oral preparation is a liquid such as mouth rinse or mouth spray which typically contains 20–99% by weight of an aqueous vehicle comprising non-toxic lower aliphatic, preferably having about 1–30% by weight alcohol such as ethanol, n-propyl, or isopropyl alcohol with the remainder water. Flavor and/or sweetener and surface active agent are also generally present. Mouth sprays also contain a suitable amount of an orally acceptable propellant materials such as a fluorocarbon, e.g. Freon or isobutane to propel the spray from a pressurized container. The CPC/Zn/ionone can also be delivered in dentifrices, gums, lozenges, breathe strips or any other technique suitable to deliver the material into the mouth.

The oral presentations should have a PH practicable for use. The pH range of about 4–9, preferably about 5–7.5, is considered the most practicable for use.

The following examples further illustrate preferred embodiments of the invention.

EXAMPLE 1

Two mouthrinse formulations were formulated. Mouthrinse A contains CPC and mouthrinse B no CPC. Each contains zinc acetate and alpha ionone. The formulations are as set out in Table 1.

TABLE 1

Mouthrinse Compositions (%)

| Ingredients | Mouthrinse A CPC/Zinc Acetate/ Alpha ionone | Mouthrinse B Zinc Acetate/ Alpha ionone |
|---|---|---|
| Ethyl Alcohol | 10.00 | 10.00 |
| Cetylpyridinium Chloride | 0.05 | 0.00 |
| Zinc Actetate Dihydrate | 0.40 | 0.40 |
| Alpha Ionone | 0.022 | 0.022 |
| Flavor | 0.198 | 0.198 |
| Glycerine | 7.50 | 7.50 |
| Sorbitol | 7.50 | 7.50 |
| Sodium Saccharin | 0.030 | 0.030 |
| Benzoic Acid | 0.05 | 0.05 |
| PEG 40 Sorbitan Diisosterate | 1.00 | 2.00 |
| Hydrochloric Acid | 0.08 | 0.08 |
| Water (Deionized/Purified) | 73.1695 | 72.2195 |
| FD&C Blue No. 1 | 0.0005 | 0.0005 |

The antibacterial effect of mouthrinses A and B was evaluated against oral bacteria by measuring maximum inhibitory dilution (MID) of the mouthrinse that inhibit bacterial growth. The results, summarized in Table 2, showed that mouthrinse A has higher MID values than mouthrinse B against representative oral bacteria which are implicated in the production of mouth malodor, plaque and gingivitis. These results clearly showed that addition of CPC to Zn acetate enhanced the antibacterial efficacy when compared to Zn acetate and alpha ionone.

Table 2 shows that addition of CPC to zinc acetate and alpha ionone provided improved antibacterial efficacy of the combination compared to zinc acetate and alpha ionone. This is an enhanced destruction of mouth bacteria in the combination of CPC and zinc. Mouthrinse A is effective in killing odorgenic bacteria at much lower concentrations is seen in the MID values.

TABLE 2

Maximum Inhibitory Dilution

| Bacterial Strain | Mouthrinse A CPC/Zinc Acetate/ Alpha ionone | Mouthrinse B Zinc Acetate/ Alpha ionone |
|---|---|---|
| Actinobacillus-Actinomycetemcomitans | 107 | 64 |
| Campylobacter recta | 128 | 24 |
| Capnocytophaga sp. | 43 | 13 |
| Eikenella corrodens | 128 | 16 |
| Fusobacterium nucleatum | 128 | 96 |
| Porphyromonas gingivalis | 256 | 128 |
| Prevotella intermedia | 427 | 235 |
| Actinomyces naeslundii | 96 | 8 |
| Actinomyces viscosus | 91 | 8 |
| Streptococcus mutans | 192 | 6 |
| Streptococcus sanguis | 64 | 24 |

EXAMPLE 2

The mouthrinses of the Table 1 also were tested clinically on volunteer subjects. Mouth odor reduction efficacy of the rinses was evaluated in two clinical studies conducted in humans. Mouth odor of the subjects was scored by human judges. The subjects rinsed in the morning after a baseline reading and then were evaluated again at 4 hours and 8 hours. The subjects rinsed again before bed and evaluated again in the next morning for the overnight scores.

subjects according to malodor scores 0 through 5.0 is equal to no odor, 1 is equal to questionable odor, 2 is equal to faint odor, 3 is equal to moderate odor, 4 is equal to strong odor and 5 is equal to very strong odor. Results of the clinical studies are summarized in Table 1. Mouthrinse B containing Zn acetate and (X-ionone significantly reduced mouth odor at 4 hours, 8 hours and overnight compared to baseline value. However, mouth odor level at each time point was above moderate odor and close to strong odor. Mouthrinse A containing CPC, Zn acetate and (alpha ionone also significantly reduced mouth odor at 4 hours, 8 hours, and overnight compared to baseline. However, in the case if mouthrinse A, mouth odor level at each time point was lower than mouthrinse B and it was in the range of the faint odor to moderate odor. The effect of mouthrinse A and B on mouth odor was also expressed in terms of percent reduction from baseline and shown as (%) next to each time point in Table 1. Results clearly showed that mouthrinse B provided higher percent reduction than mouthrinse A at each time point.

TABLE 3

| Study# | Treatment Rinse | No. of Subjects | Baseline | 4 hours | 8 hours | overnight | Significance |
|---|---|---|---|---|---|---|---|
| A | Zn Acetate/ionone | 44 | 4.19 | 3.11 (26%) | 3.27% (22%) | 3.64 (13%) | p < 0.01 |
| B | CPC/Zn acetate//ionone | 47 | 3.96 | 2.51 (37%) | 2.89% (27%) | 3.06 (22%) | p < 0.01 |

EXAMPLE 3

A randomized 2 cell double blind clinical study was conducted on 17 volunteer subjects using a placebo mouthrinse and a mouthrinse containing active ingredients 0.05% CPC, 0.4% zinc acetate and 0.022% alpha ionone. The study was directed to a reduction in volatile sulfur compounds (VCS).

The subjects had a 5 day washout period before the study and between the use of each mouthrinse. An initial baseline evaluation then was conducted. Each volunteer then rinsed their mouths with 15 mls of the assigned mouthrinse for 30 seconds. They returned in three hours for a post-treatment evaluation. Then that night prior to bed time each rinsed again with the same amount of the assigned mouthrinse for the same period of time. Each of the volunteer subjects was evaluated the following morning. The evaluations consisted of each subject keeping their mouths closed and breathing only through their nostrils for 10 minutes. A Teflon tube then was inserted through the subjects lips and two samples of breaths taken from the mouths by means of a pump. The breath samples were sent to a gas chromatograph and analyzed for the volatile sulfur compounds hydrogen sulfide, methyl mercaptan and dimethyl sulfide. These are components of breath malodor.

The three hour breath freshening results with regards to the presence of volatile sulfur compounds is given in Table 3 with overnight results given in Table 4.

TABLE 3

| Treatment Rinse | N | Initial Mean (ng/ml) | Final Mean (ng/ml) | % Reduction |
|---|---|---|---|---|
| CPC/Zn/ionone | 17 | 15.31 (±3.92) | 5.69 (±2.62) | 62.8% (p < 0.05) |
| Placebo (T) | 17 | 14.42 (±3.15) | 10.32 (±4.18) | 28.4 (p < 0.05) |

TABLE 4

| Treatment Rinse | N | Initial Mean (ng/ml) | Final Mean (ng/ml) | % Reduction |
|---|---|---|---|---|
| CPC/Zn/ionone | 17 | 15.31 (±3.92) | 7.38 (±2.71) | 51.8% (p < 0.05) |
| Placebo (T) | 17 | 14.42 (±3.15) | 13.17 (±4.02) | 8.67% (p > 0.05) |

The 3 hour and overnight results for the CPC/Zn/alpha ionone mouthrinse shows a significant improvement in the redirection of volatile sulfur compounds which are a primary component in mouth odor when zinc ions are present. The zinc ions have a synergistic affect in the reduction of mouth odor.

EXAMPLE 4

A clinical study was conducted on volunteer subjects for the decrease in oral bacteria with mouthwash that contained zinc ions CPC and alpha ionone. The concentrations were the same as in Example 3. The volunteer subjects after a 7 day washout period using a Colgate toothpaste with fluoride. The volunteer subjects then gargled 15 ml of mouthwash for 30 seconds. Each then was tested at 90 minutes and 180 minutes for the presence of *A. viscosus, S. sanguis*, and *S. mutans*. Each volunteer subject reframed from eating and drinking for the three hour period of the test. Saliva samples were taken from each volunteer subject and plated on ? media (to enumerate total salivary bacteria) and on indicator plates to enumerate odorigenic hydrogen sulfide producing bacteria. The analysis for the above bacteria was conducted using the Alamar blue fluorescence Method. The results as a percent decrease in bacteria is given in Table 5.

TABLE 5

|  | Parameter | |
|---|---|---|
|  | 90 Minutes | 180 Minutes |
| Salivary Bacteria | 59.9 | 32.1 |
| Odorigenic Bacteria | 61.7 | 72.5 |

The decrease is more evident at 90 minutes with some bacterial regenerations at 180 minutes.

We claim:

1. An oral synergistic volatile sulfur compound breath-odor controlling alcohol mouthrinse or mouthspray composition consisting essentially of an ionone terpene keytone, a non-toxic zinc compound and cetylpyridinium chloride, the ratio of zinc ions to cetylpyridinium chloride being about 1000:1 to 2:1 by weight, said zinc compound being present in the amount of about 0.01 to 5% by weight and said cetylpyridinium chloride being present in amount of about 0.0005 to 3% by weight said ionone being present in an amount of about 0.0005% to 2% by weight.

2. An oral composition as in claim 1 wherein said zinc compound is present in amount of about 0.02 to 2% by weight of zinc compound and cetylpyridinium chloride is present in amounts of about 0.001 to 1% by weight.

3. An oral composition as in claim 2 wherein said zinc compound is selected from the group consisting of zinc chloride and zinc acetate.

4. An oral composition as in claim 1 wherein said zinc compound is present in an amount of about 0.02 to 2% by weight said cetylpyridinium chloride is present in an amount of about 0.001 to 1% by weight and said ionone is present in an amount of about 0.001 to 1% by weight.

5. An oral composition as in claim 1 wherein said ionone terpene ketone is selected from the group consisting of alpha-ionone, beta-ionone, gamma-ionone, dihydroionone, alph-methylionone and ionone.

6. An oral composition as claimed in claim 5 wherein said ionone ketone terpene is alpha-ionone.

7. An oral composition as claimed in claim 1 wherein said zinc compound is selected from the group consisting of zinc chloride and zinc acetate.

8. An oral composition as claimed in claim 4 wherein said compound salt is zinc chloride.

9. An oral composition as in claim 1 wherein said ionone ketone terpene derivatives is present in a component of a flavoring oil in amounts of about 0.5 to 1% by weight of said flavoring oil.

10. An oral composition as in claim 9 wherein said flavoring oil is oil of peppermint which oil of peppermint is present in said oral composition in amounts of about 0.005 to 2% by weight.

11. A method in claim 9 wherein said ionone ketone is derivative alpha-ionone and said zinc compound is zinc chloride.

* * * * *